United States Patent [19]
Sinclair et al.

[11] Patent Number: 5,981,287
[45] Date of Patent: Nov. 9, 1999

[54] METHOD FOR THE INVESTIGATION OF HOUSE DUST

[75] Inventors: Norman Sinclair, Altenberge; Ralf Sauer, Hattingen; Heike Poch, Remscheid; Wolfgang Völker, Ladbergen, all of Germany

[73] Assignee: Vorwerk & Co. Interholding GmbH, Wuppertal, Germany

[21] Appl. No.: 08/913,973

[22] PCT Filed: Mar. 15, 1996

[86] PCT No.: PCT/EP96/01128

§ 371 Date: Feb. 2, 1998

§ 102(e) Date: Feb. 2, 1998

[87] PCT Pub. No.: WO96/30764

PCT Pub. Date: Oct. 3, 1996

[30] Foreign Application Priority Data

Mar. 24, 1995 [DE] Germany ............................ 195 10 810
May 18, 1995 [DE] Germany ............................ 195 18 287

[51] Int. Cl.$^6$ ............................ G01N 33/48; G01N 33/68
[52] U.S. Cl. ............................ 436/86; 436/164; 436/166
[58] Field of Search ............................ 436/86, 56, 63, 436/164, 166; 422/56

[56] References Cited

U.S. PATENT DOCUMENTS 5,635,132  6/1997  Blanc ...................................... 422/125
5,679,535  10/1997  Joyce et al. ............................ 422/101

FOREIGN PATENT DOCUMENTS 0345582  12/1989  European Pat. Off. .

OTHER PUBLICATIONS

Clin. Chem., vol. 31, No. 8, 1986, Washington, D.C., pp. 1551–1554, XP002008803, Watanabe, N. et al, "Urinary protein as measured with a pyrogallol red–molybdate complex, manually and in a Hitachi 726 . . .".

Patent Abstracts of Japan, Vol. 011, No. 177 (P0583), Jun. 6, 1987 & JP, A.62 006170 (Wako Pure Chem Ind Ltd). Jan. 13, 1987.

Patent Abstracts of Japan, Vol. 010, No. 358 (p–522), Dec. 2, 1986 & JP A, 61 155757 (Wako Pure Chem Ind Ltd) Jul. 15, 1986.

Anderson & Roesen, 1989, Allergy, Vol. 44, pp. 396–400.

*Primary Examiner*—Lyle A. Alexander
*Attorney, Agent, or Firm*—Martin A. Farber

[57] ABSTRACT

A invention relates to a method for the investigation of house dust with respect to a potential for inducing an allergic reaction, by mixing the house dust with a protein detector for the determination in order of size of protein-containing constituents contained in the house dust; additionally, the invention also relates a detecting agent for the estimation of a potential of house dust for inducing allergic reactions using a detection constituent for characterizing a protein component.

7 Claims, 1 Drawing Sheet

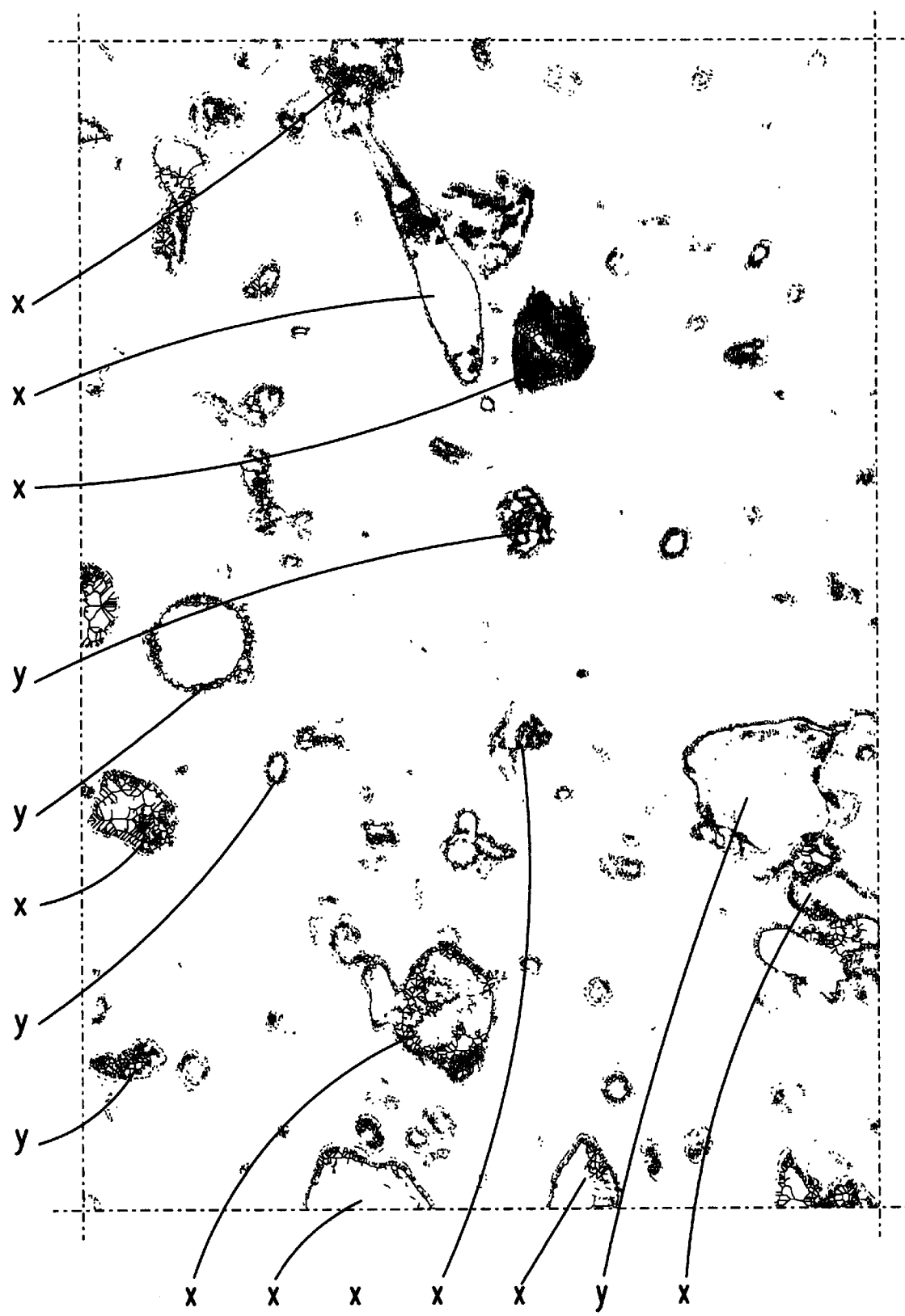

METHOD FOR THE INVESTIGATION OF HOUSE DUST

FIELD AND BACKGROUND OF THE INVENTION

The invention relates in first instance to a method for the investigation of house dust with respect to a potential for inducing allergic reactions.

It is a general observation that allergies and allergic reactions occur on a large scale and are even on the increase. Contamination present even in homes and households, such as mite excrement, moulds, pollen, certain plant fragments of grasses and birches and also epidermal scales, are held particularly responsible for this. It is attempted, using known cleaning techniques, to remove this contamination, such contamination then accumulating as constituents of the collected house dust. There is therefore a need to be able to check effective collection and removal of the house dust. There is further also a need to determine to what extent house dust on the whole, as a measurement of an allergic potential, is mixed with the above-mentioned contamination. From this, it is also possible, for example, to obtain an indication to search for particular sources of contamination.

Starting from this, a technical problem of the invention is seen as providing a method for the investigation of house dust which allows conclusions on an allergic potential of house dust to be drawn. Furthermore, a technical problem is also to be seen as providing a suitable means or a device for this purpose.

SUMMARY OF THE INVENTION

The problems pointed out are in first instance substantially solved by the subject of claim 1, wherein the house dust under investigation is treated with a protein detector for the determination in order of size of protein-containing constituents contained in the house dust. According to the invention, it has been identified that virtually all the above-mentioned allergenic constituents of house dust are made up of proteins or have protein constituents. It was further recognized that a characterization, in particular a proportional characterization of these protein-containing constituents in house dust, is simultaneously a measure of the potential of the house dust concerned for inducing allergic reactions. In further detail, it is provided that the protein detector is a dye which preferably reacts to protein-containing constituents of the house dust, in particular precipitates, by a change in colour. In this embodiment of the method, it is possible in a simple manner by means of the colour intensity to determine the proportion in order of size of the constituents of house dust which potentially induce allergic reactions. The colour intensity developed after the action of the protein detector on the house dust is used for this purpose.

In a further preferred embodiment of the process, it is provided that pyrogallol is used as a dye. Specifically, there is in question the Pyrogallol Red-Mo complex, reference to "pyrogallol" additionally including this. The use of a dye and in particular of the dye pyrogallol generally for the investigation of house dust is also considered as a—further and independent—subject of the application. In the case of pyrogallol, with respect to proteins or protein-containing particles, colouration in a violet or even blue colour shade is to be observed, while the dye itself is initially reddish. With respect to the detector, it is further recommended that the dye be dissolved in a liquid. As constituents, this liquid may in particular contain a buffer composition and preferably stabilizing additives. The buffer composition serves to prevent pH changes of the liquid leading to a premature precipitation or change in colour intensity of the dye.

In a further preferred embodiment, at least with respect to an application in which a very small amount of house dust is to be investigated, it is proposed that the liquid contain a solvent. A preferred solvent in further detail is denatured alcohol, for example 50% strength, denatured alcohol or 0.2 molar HCl/glycerol buffer mixed in the ratio 1:1 with 96% strength, denatured alcohol. At the same time, the alcohol also has the advantageous combinative effect of bringing about a decomposition of the above-mentioned constituents. Possible fatty coatings or fatty constituents can be dissolved.

The invention additionally also relates to a detecting agent for the estimation of a potential of house dust for inducing allergic reactions. This detecting agent is distinguished in that it contains a detection constituent which characterizes a protein component in the house dust. This detection constituent is preferably a dye which reacts to or precipitates on protein-containing constituents of the house dust, preferably with a colour change, it being possible to use a developing colour intensity for the determination in order of size of the proportion of these constituents. In particular, this dye may be a Pyrogallol Red-Mo complex. The detecting agent may be a liquid in which the dye is dissolved. This liquid may contain as constituents buffering agents and preferably stabilizing additives. Moreover, the liquid may contain a solvent. Reference is also made to the above embodiments.

BRIEF DESCRIPTION OF THE DRAWING

With the above and other objects and advantages in view, the present invention will become more clearly understood in connection with the detailed description of a preferred embodiment, when considered with the accompanying drawing in which the sole figure is a color micorgraph showing the invention.

DETAILED DESCRIPTION OF THE PREFERRED EMBODIMENT

A working example of an investigation liquid or of a detecting agent as is described above is composed as follows:

1. Glycine HCl as buffer constituent in the concentration 0.2 mol/l and with the pH 1.9, mixed in the ratio 1:1 with 96% strength methyl ethyl ketone-denatured alcohol.
2. The constituents 0.2 g/l of Pyrogallol Red 0.3 g/l of ammonium molybdate tetrahydrate 1.0 g/l of sodium oxalate 1.2 g/l of (L+)-tartaric acid
3. Dilution in the ratio 1:10 with 0.2 mol of HCl-glycine buffer mixed in the ratio 1:1 with 96% strength denatured alcohol.

Item 3 is used if the liquid is to be used as a reagent for colouration of house dust in a suspension. Without the additive according to item 3, the liquid may also be used as a concentrated stock solution for direct colouration, for example of filters of a vacuum cleaner.

In use, for example, 2 to 4 drops of the concentrated Pyrogallol Red-molybdenum stock solution are added dropwise to an about 1 $cm^2$ size trough-shaped filter element, which may consist of polypropylene. The filter element should be well saturated, but not covered with excess solution. Depending on the ambient temperature and amount and type of the fine dust bound into it, the dust material in the filter is coloured blue-violet, depending on the protein loading, after a maximum of 5 minutes.

Another example of use relates to the liquid diluted 1:10 with denatured 50% strength alcohol, (compare, for example, item 3 of the above working example). Approximately 1 ml of this Pyrogallol Red-molybdenum complex solution is mixed with a "knife-tipful" of house dust. By shaking the liquid, contained for example in a test tube, with warming in the hand, the colour change to blue-violet is accelerated. A violet colouring can be detected with common house dust even after 1 to 2 minutes.

Additionally, further microscopic analyses of particles from house dust characterized in this way may also be performed. The liquid or the dye do not substantially adversely affect such continuing analyses. This relates both to particles which are coloured in filters and to house dust suspensions which have been coloured with the diluted liquid.

As an annex, a copy of a micrograph obtainable in this way is shown as a single figure. On colour reproduction, the particles marked by x show a marked blue or violet colouring, while the particles marked by y have another colouring or essentially no colouring. Particles which have no colouring are, for example, grains of sand or alternatively grains of sugar.

The features disclosed in the present description, in the drawing and in the claims may be of importance both individually and in any desired combination for the realization of the invention. All features disclosed are pertinent to the invention. In the disclosure of the application, the disclosure contents of the associated/attached priority documents (copy of the prior application) are hereby also included as to their full content.

We claim:

1. Method for the investigation of house dust with respect to a potential for inducing allergic reactions, comprising the steps of mixing the house dust with a protein detector comprising pyrogallol, and determining concentration of protein-containing constituents contained in the house dust.

2. Method for the investigation of house dust comprising the steps of mixing the house dust with a protein detector and determining concentration of protein-containing constituents of the dust, wherein the protein detector is a dye which preferably precipitates on protein-containing constituents of the house dust with a colour change,, and said determining step includes observing colour intensity for a determination of the concentration.

3. Method according to claim 2, further comprising a step of dissolving the dye in a liquid containing buffer compositions and preferably stabilizing additives, the dye comprising pyrogallol.

4. Method according to claim 3 wherein the liquid contains a solvent.

5. Method according to claim 4 wherein the solvent aqueous solution of is denatured alcohol of about 50% strength.

6. Method for the investigation of house dust with respect to a potential for inducing allergic reactions, comprising the steps of mixing the house dust with a protein detector, the protein detector being a dye, and determining concentration of protein-containing constituents contained in the house dust.

7. The use of detecting agent for detecting the presence of protein in dust, wherein the detecting agent is a dye which indicates the concentration of the protein for evaluating a potential of the dust for inducing an allergic reaction.

* * * * *